United States Patent
Ouyang et al.

(10) Patent No.: US 9,964,404 B2
(45) Date of Patent: May 8, 2018

(54) FLASH THERMOGRAPHY DOUBLE WALL THICKNESS MEASUREMENT

(71) Applicant: UNITED TECHNOLOGIES CORPORATION, Hartford, CT (US)

(72) Inventors: Zhong Ouyang, Glastonbury, CT (US); David A. Raulerson, Palm Beach Gardens, FL (US); Kevin D. Smith, Glastonbury, CT (US); Hector M. Pinero, Middletown, CT (US); Jaimie Taraskevich, Tolland, CT (US); Jesse R. Boyer, Manchester, CT (US)

(73) Assignee: United Technologies Corporation, Farmington, CT (US)

( * ) Notice: Subject to any disclaimer, the term of this patent is extended or adjusted under 35 U.S.C. 154(b) by 299 days.

(21) Appl. No.: 14/765,010

(22) PCT Filed: Feb. 27, 2014

(86) PCT No.: PCT/US2014/018819
§ 371 (c)(1),
(2) Date: Jul. 31, 2015

(87) PCT Pub. No.: WO2014/134231
PCT Pub. Date: Sep. 4, 2014

(65) Prior Publication Data
US 2015/0369596 A1    Dec. 24, 2015

Related U.S. Application Data

(60) Provisional application No. 61/771,107, filed on Mar. 1, 2013.

(51) Int. Cl.
*G01B 21/08* (2006.01)
*G01J 5/00* (2006.01)
*G01N 25/00* (2006.01)

(52) U.S. Cl.
CPC .......... *G01B 21/085* (2013.01); *G01J 5/0088* (2013.01); *G01N 25/00* (2013.01); *G01J 2005/0081* (2013.01)

(58) Field of Classification Search
CPC .................................................... G01B 21/085
(Continued)

(56) References Cited

U.S. PATENT DOCUMENTS 6,394,646 B1 * 5/2002 Ringermacher ....... G01B 11/06
                                                            250/330
7,272,529 B2 * 9/2007 Hogan .................. G01B 17/02
                                                            600/446

(Continued)

FOREIGN PATENT DOCUMENTS

EP    1559500 A1    8/2005
EP    2423638 A2    2/2012

(Continued)

OTHER PUBLICATIONS

Ramirez-Granados et al ("Three-dimensional reconstruction of subsurface defects using finite-difference modeling on pulsed thermography," Appl. Opt. 51, 3153-3161 (2012), doi: 10.1364/AO.51.003153).*

(Continued)

*Primary Examiner* — Clayton E Laballe
*Assistant Examiner* — Leon W Rhodes, Jr.
(74) *Attorney, Agent, or Firm* — Carlson, Gaskey & Olds, P.C.

(57) ABSTRACT

A method of determining the thickness of an internal wall in a gas turbine engine component includes the steps of utilizing flash thermography to measure a complete thickness of a component between an outer wall and at least one enlarged cooling channel at a location where an outer cooling channel is positioned between the outer wall and the (Continued)

at least one enlarged cooling channel and where at least one member spans the cooling channel, such that the thickness is through the member which spans the outer cooling channel. An outer thickness of the component is measured from the outer wall to an outer wall of the outer cooling channel. A thickness is determined from an inner wall of the outer cooling channel to the at least one enlarged cooling channel by subtracting the measured outer thickness from the complete thickness, and also subtracting a known thickness of the outer cooling channel.

14 Claims, 3 Drawing Sheets

(58) Field of Classification Search
USPC .............................................................. 374/7
See application file for complete search history.

(56) References Cited

U.S. PATENT DOCUMENTS

| 7,775,768 | B2* | 8/2010 | Devore | F01D 5/187 |
| | | | | 416/97 R |
| 2009/0201971 | A1 | 8/2009 | Goldammer | |
| 2010/0278440 | A1 | 11/2010 | Dragovich et al. | |
| 2012/0025079 | A1 | 2/2012 | Raulerson et al. | |

FOREIGN PATENT DOCUMENTS

| WO | 9805921 A1 | 2/1998 |
| WO | 0063642 A1 | 10/2000 |

OTHER PUBLICATIONS

Goldammer, et al., "Active Thermography for Dimensional Measurements on Gas Turbine Components," Proceedings of European Conference of non-destructive testing ECNDT, pp. 1-9, Dec. 31, 2006.
Shepard, et al., "Flash Thermography of Aerospace Composites," IV Conferencia Panamericana de END Buenos Aires, pp. 1-7, Oct. 31, 2007.
International Search Report from corresponding PCT/US2014/018819, dated Jun. 10, 2014.
Supplementary European Search Report for European Application No. 14757641.7 dated Oct. 31, 2016.
Goldammer, Matthias, et al., "Active Thermography for Dimensional Measurements on Gas Turbine Components," Materials Science Forum, vol. 210-213, Dec. 31, 2006, pp. 1-9.
Walle, G., "Impuls-Video-Thermographie," Materialprüfung, Hanser, Muenchen, vol. 36, No. 3, Mar. 1, 1994, pp. 86-88.
Wu, D., et al., "Nondestructive Inspection of Turbine Blades with Lock-In Thermography," Materials Science Forum, Trans Tech Publications Ltd., vol. 210-213, Jan. 1, 1996, pp. 289-294.
International Preliminary Report on Patentability for International Application No. PCT/US2014/018819 dated Sep. 11, 2015.

* cited by examiner

FLASH THERMOGRAPHY DOUBLE WALL THICKNESS MEASUREMENT

CROSS-REFERENCE TO RELATED APPLICATION

This application claims priority to U.S. Provisional Application No. 61/771,107, filed Mar. 1, 2013.

BACKGROUND

This application relates to a method of determining a thickness of an inner wall in a gas turbine engine component.

Gas turbine engines are known and, typically, include a fan delivering air into a compressor section where it is compressed and delivered downstream into a combustor section. The air is mixed with fuel and ignited in the combustor section and products of this combustion pass downstream over turbine rotors driving them to rotate. The turbine rotors typically carry blades. Rows of static vanes are placed intermediate rows of the blades. The blades and the vanes become quite hot due to the hot products of combustion.

Thus, it is known to provide cooling channels within the gas turbine engine components. The blades and the vanes typically include an airfoil receiving the cooling channels. Historically, there were relatively large central cooling channels. A wall thickness between an outer wall of the airfoil and the channel must be carefully maintained and designed.

It was known in the art to provide various inspection means for measuring a thickness between the outer wall and the cooling channels in manufactured airfoils to ensure that it meets the design specifications. One method of measuring the wall thickness was flash thermography.

Flash thermography is a known method of measuring thickness or looking for flaws within a body. Essentially, a flash of light energy is directed off a component to be inspected. This dramatically and quickly raises the temperature of the component. An infrared camera repeatedly captures images of the surface and can determine changes in the heat at the surface. Modern flash thermography systems are able to evaluate those changes on a pixel by pixel basis and, thus, can provide temperature change information over very precise areas on the surface of the component.

Those changes can be translated to a thickness in the component based upon the material of the component and utilizing algorithms well known in the art.

More recently, gas turbine engine components having airfoils have been provided with so-called cooling channels. The cooling circuits are precisely made to an exact width and have sometimes been placed between an outer wall and the relatively larger central cooling channels.

Flash thermography is not able to provide accurate measurements of the distance from an inner wall of the microcircuit to the enlarged central cooling channel.

SUMMARY

In a featured embodiment, a method of determining the thickness of an internal wall in a gas turbine engine component includes the steps of utilizing flash thermography to measure a complete thickness of a component between an outer wall and at least one enlarged cooling channel at a location where an outer cooling channel is positioned between the outer wall and the at least one enlarged cooling channel and where at least one member spans the outer cooling channel, such that the thickness is through the member which spans the outer cooling channel. An outer thickness of said component is measured from the outer wall to an outer wall of the outer cooling channel. A thickness is determined from an inner wall of the outer cooling channel to the at least one enlarged cooling channel by subtracting the measured outer thickness from the complete thickness, and also subtracting a known thickness of the outer cooling channel.

In another embodiment according to the previous embodiment, a high emissivity outer layer is provided on the outer wall prior to the flash thermography.

In another embodiment according to any of the previous embodiments, the flash thermography includes directing a flash of light at the outer wall of the component and then capturing images over time at an infrared camera to determine a change in heat at the outer wall at different surface locations.

In another embodiment according to any of the previous embodiments, the change in heat is determined on a pixel by pixel basis.

In another embodiment according to any of the previous embodiments, the measured outer thickness is measured at a second location generally aligned on the outer wall of the component, but spaced in a radial direction from a location at which the member spans the outer cooling channel, and where there is a space between the inner wall and outer wall of the outer cooling channel.

In another embodiment according to any of the previous embodiments, the measured complete thickness and measured outer thickness are taken at locations spaced from each other between a trailing edge and a leading edge of the component.

In another embodiment according to any of the previous embodiments, the component includes an airfoil with at least one enlarged cooling channel and the outer cooling channel.

In another embodiment according to any of the previous embodiments, the outer cooling channel is a microcircuit cooling channel.

In another embodiment according to any of the previous embodiments, a method of determining the thickness of an internal wall in a gas turbine engine airfoil including an outer cooling channel includes the steps of utilizing flash thermography to measure a complete thickness between an outer wall and at least one enlarged cooling channel at a location where an outer cooling channel is positioned between the outer wall and the at least one enlarged cooling channel and where at least one member spans the outer cooling channel such that the thickness is through the member which spans the outer cooling channel. An outer thickness is measured from the outer wall to an outer wall of the outer cooling channel. A thickness is determined from an inner wall of the outer cooling channel to at least one enlarged cooling channel by subtracting the measured outer thickness from the complete thickness, and also subtracting a known thickness of the outer cooling channel.

In another embodiment according to the previous embodiments, a high emissivity outer layer is provided on the outer wall prior to the flash thermography.

In another embodiment according to any of the previous embodiments, the flash thermography includes directing a flash of light at the outer wall and then capturing images over time at an infrared camera to determine a change in heat at the outer wall at different surface locations.

In another embodiment according to any of the previous embodiments, the change in heat is determined on a pixel by pixel basis.

In another embodiment according to any of the previous embodiments, the measured outer thickness is measured at a second location generally aligned on the outer wall, but spaced in a radial direction from a location at which the member spans the outer cooling channel, and where there is a space between the inner wall and outer wall of the outer cooling channel.

In another embodiment according to any of the previous embodiments, the outer cooling channel is a microcircuit cooling channel.

These and other features may be best understood from the following drawings and specification.

DETAILED DESCRIPTION

Figure 1A:
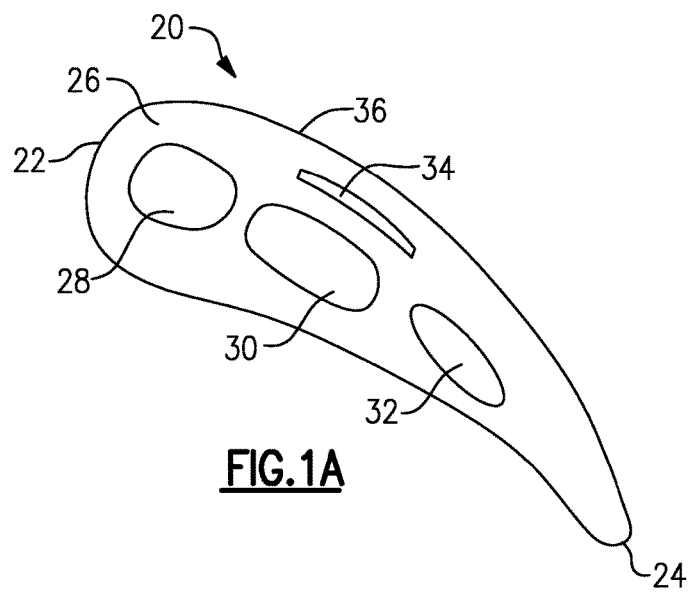
FIG. 1A shows an airfoil which may be incorporated into a gas turbine engine.

A component having an airfoil 20 which may be a turbine blade or vane for use in a gas turbine engine, is illustrated in FIG. 1A. As shown, the airfoil 20 extends from a leading edge 22 to a trailing edge 24 and has a body 26 with enlarged central cooling channels 28, 30 and 32. As can be appreciated, this is a cross-section through the airfoil 20 and the channels 28, 30 and 32 would be generally closed off at a radially outer end, and there would be a platform for mounting the blade at a radially inner end. In the case of a vane, there may be platforms at each of a radially inner and a radially outer end in some embodiments.

One side wall 36 of the airfoil 20 is illustrated receiving a microcircuit cooling channel 34. The microcircuit cooling channel 34 is aligned with the channel 30. In practice, the airfoil 20 may have microcircuit cooling channels on both sides of the airfoil, and may even have microcircuit cooling channels associated with each of the enlarged central cooling channels 28, 30 and 32. However, for purposes of understanding this invention, we need consider only one microcircuit cooling channel 34.

Figure 1B:
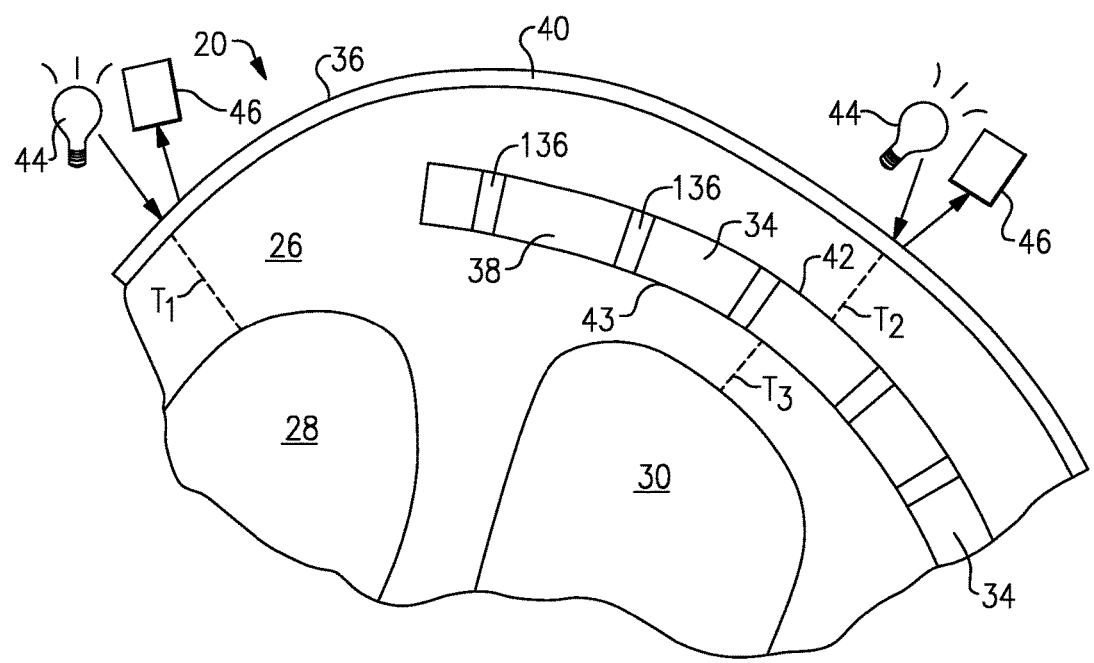
FIG. 1B is an enlarged view of a portion of the airfoil.

As shown in FIG. 1B, a flash thermography inspection operation is being utilized on the airfoil 20. As known, a light pulse from a light source 44 is directed off an outer surface 36 of the airfoil body 26. A high emissivity paint 40 may be applied to the outer surface 36 to increase the heat absorption from that light source 44 into the body 26. The light pulse whose width was controlled by quench circuit and computer need only last a few milliseconds.

As the part cools, an infrared camera 46 captures information as shown schematically. The camera 46 can evaluate the heat change on a pixel by pixel basis and, thus, can determine a thickness $T_1$ between the outer wall 36 and the cooling channel 28. Any number of known algorithms can be utilized to calculate the thickness $T_1$.

Challenges arise, however, when there are two internal cavities, such as when a microcircuit cooling channel 34 is aligned with an enlarged central cooling channel 30. The flash thermography method can be utilized to determine the thickness between the outer wall 36 and an outer side 42 of the microcircuit cooling channel 34. This is shown as $T_2$. However, flash thermography can provide no information about the thickness $T_3$ between the inner wall 43 of the microcircuit cooling channel 34 and the outer wall of the central cooling channel 30.

The present invention provides a method of determining the thickness $T_3$.

Figure 1C:
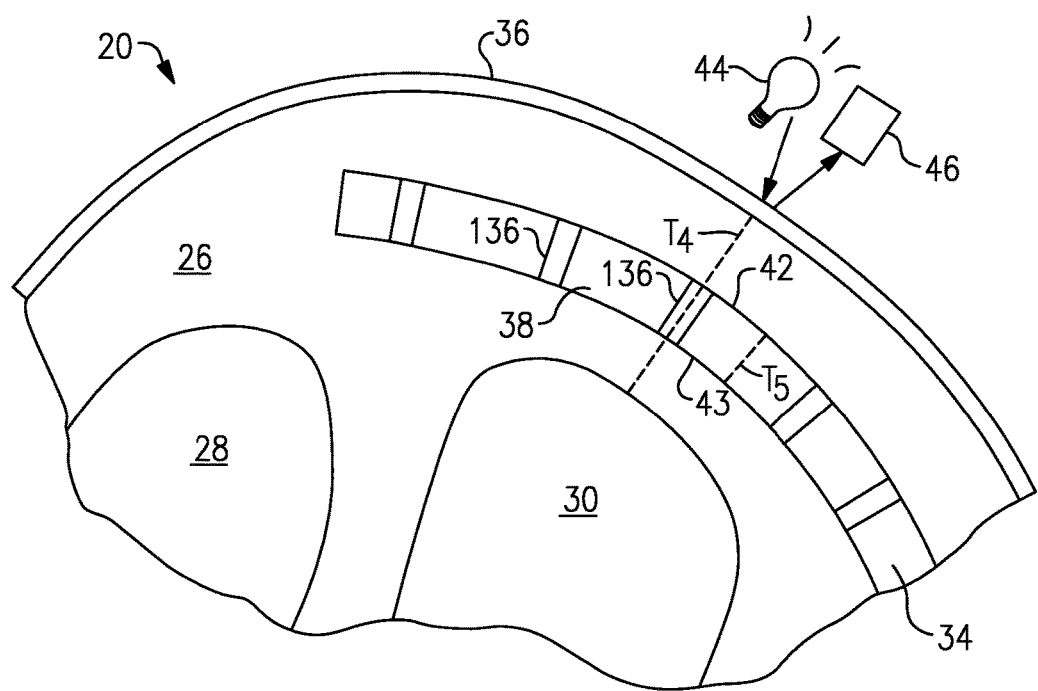
FIG. 1C shows a method being performed on the same portion as shown in FIG. 1B.

As shown in FIG. 1C, a thickness $T_4$ is measured from the outer wall 36 through any one of a plurality of pedestals or ribs 136, which extend across the microcircuit cooling channel 34 between the surfaces 42 and 43. Flash thermography is utilized to determine $T_4$.

A thickness $T_5$, which is the radial thickness of the microcircuit, is closely controlled and known.

Figure 2A:
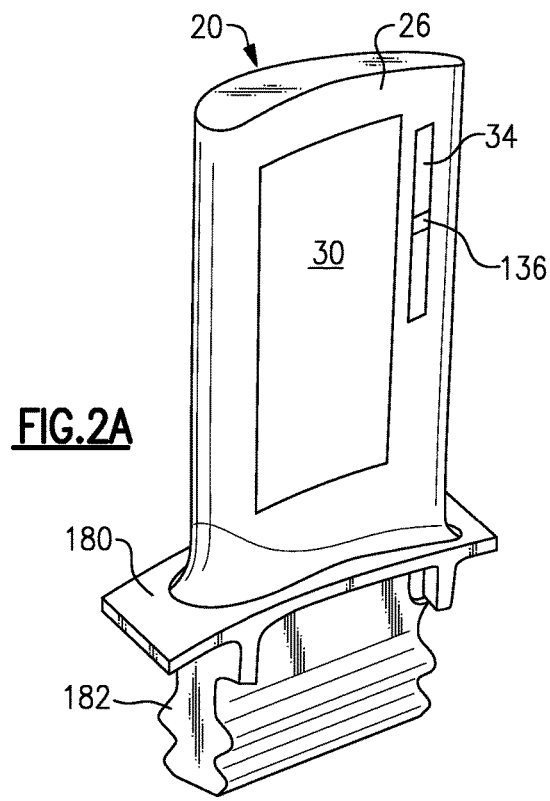
FIG. 2A shows an alternative method.
Figure 2B:
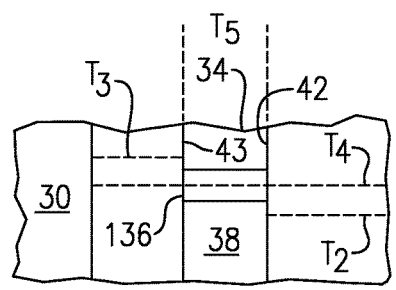
FIG. 2B shows a detail of FIG. 2A.

FIGS. 2A and 2B show an alternative, wherein the thickness $T_2$ is measured at a location aligned with the location of the thickness $T_4$. As can be appreciated from FIG. 2A, the rib or pedestal 136 does not extend throughout the entire radial length of the body 26, but is relatively limited. As shown in FIG. 2B, the thickness $T_2$ may be taken radially spaced from the rib 136, but otherwise at an aligned location. By selecting radially spaced locations to measure the thicknesses $T_2$ and $T_4$, it more likely that the thickness $T_3$ will be the same for the two locations. The selection of the relative locations for the measurements of $T_2$ and $T_4$ may be as shown in FIGS. 1B and C or as FIG. 2 depending on the overall shape of the airfoil.

Figure 3:
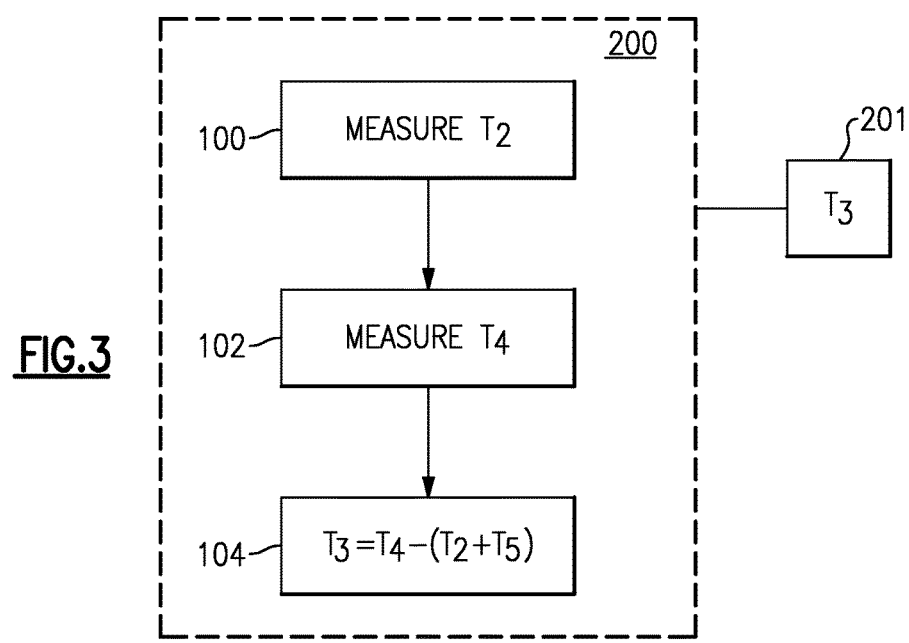
FIG. 3 is a flow chart.

Now, once the thickness of $T_2$ and $T_4$ are known, FIG. 3 shows a method of calculating the thickness $T_3$. As shown as step 100, $T_2$ is measured and then $T_4$ is measured at 102. As shown at step 104, $T_3$ is simply the $T_4$ measurement minus the sum of $T_2$ and the known thickness $T_5$ of the microcircuit cooling channel 34.

In this manner a method is provided which accurately determines the thickness $T_3$.

As can be appreciated, the infrared camera 46 may include a computer, or it may communicate with a computer to provide the measurements of steps 100, 102 and 104. This is shown schematically in FIG. 3 by the dotted outline 200, which is representative of a computer for performing the method. Notably, the computer 200 provides an output 201, which may be a display of the determined $T_3$.

While the method of this disclosure has been disclosed for a component including a microcircuit cooling channel 34, the teachings would extend to other outer cooling channels positioned between an enlarged internal cooling channel and the outer wall.

Although an embodiment of this disclosure has been disclosed, a worker of ordinary skill in this art would recognize that certain modifications would come within the scope of this disclosure. For that reason, the following claims should be studied to determine the true scope and content of this disclosure.

The invention claimed is:

1. A method of determining the thickness of an internal wall in a gas turbine engine component comprising the steps of:
   (a) utilizing flash thermography to measure a complete thickness of a component between an outer wall and at least one enlarged cooling channel at a location where an outer cooling channel is positioned between said outer wall and the at least one enlarged cooling channel and where at least one member spans said outer cooling channel, such that said complete thickness is measured through said member which spans said outer cooling channel; and
   (b) measuring an outer thickness of said component from said outer wall to an outer wall of said outer cooling channel, and determining a thickness from an inner wall of said outer cooling channel to said at least one enlarged cooling channel by subtracting said measured outer thickness from said complete thickness, and also subtracting a known thickness of said outer cooling channel.

2. The method as set forth in claim 1, wherein a high emissivity outer layer is provided on said outer wall prior to said flash thermography.

3. The method as set forth in claim 1, wherein said flash thermography includes directing a flash of light at the outer wall of said component and then capturing images over time at an infrared camera to determine a change in heat at said outer wall at different surface locations.

4. The method as set forth in claim 3, wherein said change in heat is determined on a pixel by pixel basis.

5. The method as set forth in claim 1, wherein said measured outer thickness is measured at a second said location generally aligned on said outer wall of said component, but spaced in a radial direction from a location at which said member spans said outer cooling channel, and where there is a space between the inner wall and outer wall of said outer cooling channel.

6. The method as set forth in claim 1, wherein said measured complete thickness and measured outer thickness are taken at locations spaced from each other between a trailing edge and a leading edge of said component.

7. The method as set forth in claim 1, wherein said component includes an airfoil with said at least one enlarged cooling channel and said outer cooling channel.

8. The method as set forth in claim 1, wherein said outer cooling channel is a microcircuit cooling channel.

9. A method of determining the thickness of an internal wall in a gas turbine engine airfoil including an outer cooling channel comprising the steps of:
  (a) utilizing flash thermography to measure a complete thickness between an outer wall and at least one enlarged cooling channel at a location where an outer cooling channel is positioned between said outer wall and the at least one enlarged cooling channel and where at least one member spans said outer cooling channel, such that said complete thickness is measured through said member which spans said outer cooling channel; and
  (b) measuring an outer thickness from said outer wall to an outer wall of said outer cooling channel, and determining a thickness from an inner wall of said outer cooling channel to said at least one enlarged cooling channel by subtracting said measured outer thickness from said complete thickness, and also subtracting a known thickness of said outer cooling channel.

10. The method as set forth in claim 9, wherein a high emissivity outer layer is provided on said outer wall prior to said flash thermography.

11. The method as set forth in claim 9, wherein said flash thermography includes directing a flash of light at the outer wall and then capturing images over time at an infrared camera to determine a change in heat at said outer wall at different surface locations.

12. The method as set forth in claim 11, wherein said change in heat is determined on a pixel by pixel basis.

13. The method as set forth in claim 9, wherein said measured outer thickness is measured at a second said location generally aligned on said outer wall, but spaced in a radial direction from a location at which said member spans said outer cooling channel, and where there is a space between the inner wall and outer wall of said outer cooling channel.

14. The method as set forth in claim 9, wherein said outer cooling channel is a microcircuit cooling channel.

\* \* \* \* \*